United States Patent [19]

Schroeder et al.

[11] Patent Number: 4,973,552
[45] Date of Patent: Nov. 27, 1990

[54] STAUROSPORINE FERMENTATION PROCESS

[75] Inventors: Daniel R. Schroeder, Higganum; Kin S. Lam, Cheshire; Jacqueline M. Mattei, East Haven; Grace A. Hesler, Branford, all of Conn.

[73] Assignee: Bristol-Meyers Squibb Company, New York, N.Y.

[21] Appl. No.: 482,390

[22] Filed: Feb. 20, 1990

[51] Int. Cl.$^5$ .......................... C12P 17/18; C12R 1/55
[52] U.S. Cl. ...................................... 435/119; 435/898
[58] Field of Search ................................ 435/119, 898

[56] References Cited
PUBLICATIONS

CA 106:43722m, Oka et al., Agric Biol. Chem. 1986 50(11) 2723.7.
J. Chem. Soc. Chem. Comm. 1978: 800–801, 1978.

Primary Examiner—Herbert J. Lilling
Attorney, Agent, or Firm—David M. Morse

[57] ABSTRACT

A fermentation process for preparing staurosporine, a known antibiotic, employing a heretofore unknown micrrorganism is described, said microorganism being classified as a novel strain of *Streptomyces hygroscopicus* being and herein designated *Streptomyces hygroscopicus* strain C39280-450-9 (ATCC 53730).

1 Claim, No Drawings

STAUROSPORINE FERMENTATION PROCESS

BACKGROUND OF THE INVENTION

Field of the Invention

This invention relates to a new microbiological process for preparation of the alkaloid compound staurosporine. 2. Description of the Prior Art Staurosporine is a known alkaloid compound having the structure

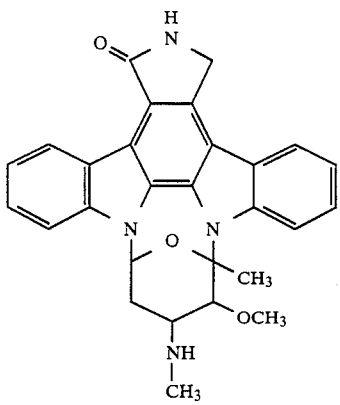

Pat. No. 4,107,297 discloses preparation of staurosporine (designated as AM-2282 in the reference) by fermentation of *Streptomyces staurosporeus* nov. sp. NRRL 11.184. Information on the molecular structure of staurosporine is available in *J. Chem. Soc. Chem. Comm.* 1978: 800–801, 1978.

Staurosporine is known to have antimicrobial activity (primarily against yeast and fungi) and is also reported to have hypotensive activity. U.S. Pat. No. 4,735.039 discloses that staurosporine also has insecticidal activity.

SUMMARY OF THE INVENTION

The present invention relates to a new microbiological process for the preparation of staurosporine. The new process comprises cultivating a staurosporine-producing strain of *Streptomyces hygroscopicus*, most preferably *Streptomyces hygroscopicus* strain C39280-450-9 (ATCC 53730) or a staurosporine-producing mutant or variant thereof, in an aqueous nutrient medium containing assimilable sources of carbon and nitrogen under submerged aerobic conditions until a substantial amount of staurosporine is produced by said organism in said culture medium and then recovering the staurosporine from said culture medium.

DETAILED DESCRIPTION

The preferred staurosporine-producing organism of the present invention is a novel strain of *Streptomyces hygroscopicus* designated herein as *Streptomyces hygroscopicus* strain C39280-450-9. This strain was isolated from a soil sample collected at Numazu prefecture, Japan. A biologically pure culture of strain C39280-450-9 has been deposited with the American Type Culture Collection. Rockville, Md., and added to their permanent collection of microorganisms as ATCC 53730. This culture, designated as C39280. is also maintained as a dormant culture in lyophile tubes and cryogenic vials in the Bristol-Myers Squibb Pharmaceutical Research and Development Division Culture Collection, 5 Research Parkway, Wallingford, Conn., 06492.

The results of taxonomic studies performed on strain C39280-450-9 indicate that the strain is a novel strain of *Streptomyces hygroscopicus*. Strain C39280-450-9 has the following properties as determined by materials and procedures described by Shirling & Gottlieb (Int. J. Sept. Bacteriology 16: 313–340, 1966; ibid. 18: 69–189, 1968; ibid. 22: 265–394, 1972), Staneck & Roberts (Appl. Miccrobiol. 28: 226–31, 1974), K.P. Schaal (M. Goodfellow and D.E. Minnikin Eds., Chemical Methods in Bacterial Systematics, Academic Press Inc., pp. 359–381, 1985).

MORPHOLOGY

Morphological characteristics of strain C39280-450-9 include: (1) the formation of non-fragmenting substrate and aerial mycelia, (2) spiral chains of arthrospores borne from branched sporophores on the aerial mycelium, the spore chains having 2 to 6 turns. (3) smooth spore ornamentation.

CULTURAL AND PHYSIOLOGICAL CHARACTERISTICS

Cultural characteristics as observed on descriptive media are summarized in Table 1. Hygroscopic change is evident in ISP medium no. 4 and Modified Bennett's medium. Soluble potato starch and glucose are utilized for growth. Utilization of inositol is questionable. Physiological characteristics are summarized in Table 2.

CELL WALL CHEMISTRY

Analysis of strain C39280-450-9 whole cell hydrolysates revealed LL-diaminopimelic acid, galactose, ribose, and mannose as cell wall components, hence the organism's Type I cell wall assignment. Phospholipid analysis detected the presence of phosphatidyl ethanolamine and phosphatidyl glycerol, typing the phospholipid pattern as PII.

TABLE 1

Cultural Characteristics of Strain C39280-450-9

| Agar medium | Growth | Reverse color | Aerial mycelium | Pigment |
| --- | --- | --- | --- | --- |
| ISP 2 | moderate | colorless | moderate | oxide yellow, 5C7 |
| ISP 3 | good | colorless | abundant, light gray | none |
| ISP 4 | moderate | colorless | scant, hygroscopic | none |
| ISP 5 | poor | colorless | brownish gray, 6F2 | none |
| ISP 6 | poor | colorless | none | none |
| ISP 7 | poor | colorless | none | none |
| Glucose - Asparagine | moderate | cream | none | none |
| Czapek's Sucrose - Nitrate | scant | colorless | none | none |
| Nutrient | poor | yellowish white, 3A2 | none | none |
| Modified Bennett's | moderate | colorless | moderate, hygroscopic | none |
| Thin Potato Carrot | poor | | moderate gray and white | none |
| ATCC 5 | moderate | colorless | moderate, gray | none |
| ATCC 172 | moderate | colorless | moderate, white and gray, 2B1 | none |
| Potato-Dextrose | poor | colorless | fair; white and gray | none |
| Tomato | good | grayish | none | none |

TABLE 1-continued

| Cultural Characteristics of Strain C39280-450-9 | | | | |
|---|---|---|---|---|
| Agar medium | Growth | Reverse color | Aerial mycelium | Pigment |
| Juice | | orange, 5B4 | | |
| Tryptic Soy | poor | yellowish white, 3A2 | none | none |
| Xanthine | scant | yellowish white, 3A2 | none | none |

Color names and numbers from A. Kornerup and J. H. Wanscher, Reinhold Color Atlas, Reinhold Publishing Corporation, Copenhaen, Denmark, 1961.

TABLE 2

| Physiological Characteristics of Strain C39280-450-9 | |
|---|---|
| Growth temperature | 10° C.–37° C. |
| pH tolerance | 5.5–9 |
| NaCl tolerance | 1%–8% |
| Gelatin liquefaction | + |
| Starch hydrolysis | + |
| Urease | + |
| Milk coagulation | − |
| peptonization | + |
| Nitrate reduction | − |
| Lysozyme | − |

The morphological characteristics and cell chemistry of strain C39280-450-9 classify it as a Streptomyces species. Further classification as a *Streptomyces hygroscopicus* species is corroborated by the clustering of the organism's spiral spore chains and subsequent hygroscopic properties.

It is to be understood that for the production of staurosporine according to the present invention, limitation to the specific preferred strain described above is not intended. It is specifically desired and intended to include within the scope of the invention other staurosporine-producing strains of *Streptomyces hygroscopicus*, particularly variants or mutants of the deposited strain produced by known procedures such as irradiation with x-rays or ultraviolet light, treatment with nitrogen mustards, phage exposure, and the like.

PREPARATION OF STAUROSPORINE

Staurosporine may be prepared according to the present invention by cultivating a staurosporine-producing strain of *Streptomyces hygroscopicus*, preferably a strain of *Streptomyces hygroscopicus* having the identifying characteristics of strain C39280-450-9 (ATCC 53730) or a mutant or variant thereof, in a conventional aqueous nutrient medium. The organism is grown in a nutrient medium containing known nutritional sources for actinomycetes, i.e. assimilable sources of carbon and nitrogen plus optional inorganic salts and other known growth factors. Submerged aerobic conditions are preferably employed for the production of large quantities of antibiotic, although for production of limited amounts, surface cultures and bottles may also be used. The general procedures used for the cultivation of other actinomycetes are applicable to the present invention.

The nutrient medium should contain an appropriate carbon source such as sucrose, lactose, glucose, rhamnose, fructose, glycerol or soluble starch. An assimilable nitrogen source such as fish meal, peptone, peanut meal, cottonseed meal or cornsteep liquor should also be employed. Nutrient inorganic salts can also be incorporated in the medium so as to provide sodium, potassium, ammonium, calcium, phosphate, sulfate, chloride, bromide, nitrate, carbonate and like ions.

Production of staurosporine can be effected at any temperature conducive to satisfactory growth of the producing organism, e.g. 10° to 37° C. and is conveniently carried out at a temperature of about 28° C. The fermentation may be carried out in flasks or in laboratory or industrial fermentors of various capacity. When tank fermentation is to be used, it is desirable to produce a vegetative inoculum in a nutrient broth by inoculating a small volume of the culture medium with a slant or lyophilized culture of the producing organism. After obtaining a viable and active inoculum in this manner, it is transferred aseptically to the fermentation tank charged with production medium for large scale production of staurosporine. The medium in which the vegetative inoculum is prepared can be the same as, or different from, that utilized in the tank as long as it is such that a good growth of the producing organism is obtained. Agitation during the fermentation may be provided by a mechanical impeller. Antifoam agents such as lard oil or silicone oil may be added if needed. Antibiotic production may be monitored by high performance liquid chromatography (HPLC) assay or by a conventional biological assay.

After optimal broth potency has been obtained, the staurosporine may be recovered from the culture medium by conventional extraction and chromatographic techniques such as described in Example 4 below.

Staurosporine obtained by the method of the present invention exhibits characteristics identical to those of the known antibiotic as described in the literature.

The following examples are offered only for the purpose of illustrating the present invention and are not intended to limit the scope of the invention in any respect.

EXAMPLE 1

PREPARATION OF CRYOPRESERVATIVE CULTURE OF STRAIN C39280-450-9

Strain C39280-450-9 was maintained as a cryopreservative culture stored at −80° C. in a Revco ultralow temperature freezer. To prepare a cryopreservative culture, strain C39280-450-9 was transferred in test tubes on agar slants of ISP medium no. 4 (Difco).

The agar slant was incubated at 28° C. for 14 days. Vegetative culture was prepared by transferring the surface growth from the slant culture to a 500 ml Erlenmeyer flask containing 100 ml of a sterile vegetative medium consisting of

| | |
|---|---|
| Glucose | 20 g |
| Peptone | 5 g |
| Fishmeat extract | 5 g |
| Yeast extract | 3 g |
| CaCO$_3$ | 4 g |
| Deionized water | q.s. to 1 liter |

This vegetative culture was incubated at 28° C. for 72 hours on a rotary shaker set at 230 rpm. The vegetative culture was mixed with an equal volume of cryoprotective solution consisting of

| | |
|---|---|
| Sucrose | 100 g |
| Glycerol | 200 g |
| Deionized water | q.s. to 1 liter |

Five ml portions of this mixture were transferred to sterile cryogenic tubes (Nunc) and were frozen in a dry ice-acetone bath. The frozen vegetative cultures were then stored at −80° C. in a Revco ultralow temperature freezer.

EXAMPLE 2

PREPARATION OF VEGETATIVE CULTURE OF STRAIN C39280-450-9

Vegetative culture was prepared by transferring 5 ml of the cryopreservative culture to a 500 ml Erlenmeyer flask containing 100 ml of a sterile vegetative medium having the same composition as the vegetative medium described in Example 1. The vegetative culture was incubated at 28° C. for 72 hours on a rotary shaker set at 250 rev/min.

EXAMPLE 3

FERMENTATION OF STAUROSPORINE IN SHAKE FLASK CULTURE

Four ml of vegetative culture prepared according to the procedure of Example 2 was inoculated into 500 ml Erlenmeyer flasks each containing 100 ml of a production medium consisting of:

| Glucose | 30 g |
| Nutrisoy | 15 g |
| $CaCO_3$ | 4 g |
| Deionized water | q.s. to 1 liter |

The production culture was incubated at 28° C. on a rotary shaker set at 250 rev/min. The production of staurosporine was monitored by HPLC analysis. Optimal production of 130 μg/ml was reached at 6 days of fermentation.

EXAMPLE 4

ISOLATION AND PURIFICATION OF STAUROSPORINE

Whole broth (10 l) obtained according to the general procedure of Example 3 was filtered using Dicalite filter aid. The mycelial mat, after stirring in tetrahydrofuran (THF) (2 liters) for one hour, was filtered and rinsed with an additional volume of acetone (1 liter). The filtrate was concentrated under reduced pressure to an aqueous layer, the volume increased with brine (1 liter), and the aqueous layer extracted with chloroform (1 liter, 2×) to yield 45 g of crude extract.

The $CHCl_3$-$CH_3OH$-THF (1:1:1v/v) soluble materials from the crude extract were absorbed on 16 g silica gel (Lichroprep Si 60 40–63 μm, EM Science) and applied to a 150 ml VLC (vacuum liquid chromatography) funnel containing an additional 54 g silica gel. A hexane-THF step gradient was carried out. Semi-purified staurosporine eluted with hexane-THF (1:4 v/v). The combined fractions weighed three grams.

Further purification was done on Sephadex LH-20. The advanced fraction was dissolved in $CHCl_3$-$CH_3OH$-THF (1:1:1 v/v) and applied to a column equilibrated with THF-$CHCl_3$(2:1 v/v). Flow rate was 1.3 ml/min. Staurosporine eluted at three-fourths bed volume (1.4 g). This material was applied to a second LH-20 column equilibrated with THF. Staurosporine (1.16 g) eluted at one bed volume.

Staurosporine obtained by the above procedure was identical in all respects ($^1$H-NMR, $^{13}$C-NMR, UV, IR, Mass Spec., HPLC RP-$C_{18}$) to published physicochemical data for staurosporine.

What is claimed is:

1. A process for the production of staurosporine which comprises cultivating a staurosporine-producing strain of Streptomyces hygroscopicus in an aqueous nutrient medium under submerged aerobic conditions until a substantial amount of staurosporine is produced by said organism in said culture medium and recovering the staurosporine from the culture medium substantially free of co-produced substances wherein the organism is *Steptomyces hygroscopicus* strain C3920-450-9 (ATCC 53730), a mutant or variant thereof.

* * * * *